(12) United States Patent
Takahashi et al.

(10) Patent No.: US 10,625,099 B2
(45) Date of Patent: Apr. 21, 2020

(54) RADIOTHERAPY TRACKING APPARATUS

(71) Applicant: SHIMADZU CORPORATION, Kyoto (JP)

(72) Inventors: Wataru Takahashi, Kyoto (JP); Michel Dargis, Quebec (CA); Shinichiro Mori, Chiba (JP)

(73) Assignee: SHIMADZU CORPORATION, Kyoto (JP)

( * ) Notice: Subject to any disclaimer, the term of this patent is extended or adjusted under 35 U.S.C. 154(b) by 130 days.

(21) Appl. No.: 16/107,368

(22) Filed: Aug. 21, 2018

(65) Prior Publication Data

US 2019/0060672 A1    Feb. 28, 2019

(30) Foreign Application Priority Data

Aug. 23, 2017    (JP) .................. 2017-160108

(51) Int. Cl.
  *A61N 5/10*    (2006.01)
  *A61B 6/00*    (2006.01)
  *A61B 6/12*    (2006.01)

(52) U.S. Cl.
  CPC .............. *A61N 5/1049* (2013.01); *A61B 6/12* (2013.01); *A61B 6/487* (2013.01); *A61B 6/541* (2013.01); *A61B 6/548* (2013.01); *A61N 5/1067* (2013.01); *A61N 2005/1061* (2013.01)

(58) Field of Classification Search
  CPC .......... A61N 5/1049; A61N 2005/1061; A61N 5/1067; A61B 6/487; A61B 6/541; A61B 6/12; A61B 6/548
  USPC ........................................................ 378/65
  See application file for complete search history.

(56) References Cited

U.S. PATENT DOCUMENTS

| 6,307,914 B1* | 10/2001 | Kunieda .................. A61B 6/12 378/65 |
| 2008/0221439 A1* | 9/2008 | Iddan ..................... A61B 90/37 600/424 |
| 2008/0221442 A1* | 9/2008 | Tolkowsky ............ A61B 90/37 600/425 |
| 2011/0164035 A1* | 7/2011 | Liao ........................ G06T 7/246 345/419 |

(Continued)

FOREIGN PATENT DOCUMENTS

JP    3053389    6/2000

*Primary Examiner* — David P Porta
*Assistant Examiner* — Gisselle M Gutierrez
(74) *Attorney, Agent, or Firm* — Andrew F. Young, Esq.; Lackenbach Siegel, LLP

(57) ABSTRACT

A radiotherapy tracking apparatus for tracking a position of a specific region with markerless tracking even when visual recognition of the specific region of the subject is poor and for eliminating preliminary work such as preparation of a template. A control element comprises a DRR image generation element, a phase-based position calculation element, an X-ray fluoroscopic image obtaining element, a phase adjuster, a frame-based position calculation element, a gating element and a memory storage. The frame-based position calculation element calculates the position of the specific region of the subject in the X-ray fluoroscopic image having the plurality of frames frame-by-frame based on the DRR image adjusted with the X-ray fluoroscopic image in the phase adjustment element and the position of the specific region calculated by the phase-based position calculation element.

5 Claims, 5 Drawing Sheets

(56) References Cited

U.S. PATENT DOCUMENTS

| | | | |
|---|---|---|---|
| 2012/0106704 A1* | 5/2012 | Maurer, Jr. | G06F 19/3481 |
| | | | 378/65 |
| 2014/0114308 A1* | 4/2014 | Tolkowsky | A61B 90/37 |
| | | | 606/41 |
| 2014/0114333 A1* | 4/2014 | Tolkowsky | A61B 90/37 |
| | | | 606/159 |
| 2014/0371513 A1* | 12/2014 | Maurer, Jr. | G06F 19/3481 |
| | | | 600/1 |
| 2015/0283319 A1* | 10/2015 | Tolkowsky | A61B 90/37 |
| | | | 600/431 |
| 2020/0009404 A1* | 1/2020 | Fujii | A61N 5/1049 |

* cited by examiner

RADIOTHERAPY TRACKING APPARATUS

CROSS REFERENCE TO RELATED APPLICATIONS

This application relates to, and claims priority from JP 2017-160108 filed Aug. 23, 2017, the entire contents of which are incorporated herein by reference.

FIGURE SELECTED FOR PUBLICATION

FIG. 2.

BACKGROUND OF THE INVENTION

Field of the Invention

The present invention relates to a radiotherapy tracking apparatus (tracking apparatus for radiotherapy), which detects respiratory phases of a subject and tracks movement of a specific region of the subject.

Description of the Related Art

The radiation relative to a radiotherapy, in which the radiation including an X-ray and an electron beam and so forth is irradiated to an affected area including tumor and so forth, must be accurately irradiated to the affected area. Nevertheless, in some cases, not only the subject may unintentionally move the body thereof, but also the affected area per se may move. For example, a tumor near the lung largely moves depending on breathing. Accordingly, a radiation irradiation device of marker tracking method having an aspect, in which the irradiation timing of the therapeutic beam is controlled while detecting the position of the spherical metal maker implanted (inserted) near a tumor by an X-ray fluoroscopic device, is disclosed (referring to Patent Document 1).

According to such radiation irradiation device, the fiducial marker implanted inside the body is radiographed using a first X-ray fluoroscopic mechanism comprising a first X-ray tube and a first X-ray detector and the second X-ray fluoroscopic mechanism comprising a second X-ray tube and a second X-ray detector and a three-dimensional positional information (data) is obtained utilizing the two-dimensional fluoroscopic radiograph provided by the first X-ray fluoroscopic mechanism and the two-dimensional fluoroscopic radiograph provided by the second X-ray fluoroscopic mechanism. Subsequently, the maker of the region accompanying movement can be detected with a high-degree of accuracy by continuously performing the X-ray fluoroscopy and calculating the real-time three-dimensional and positional information of the marker. And, an irradiation timing of the therapeutic beam is controlled based on the positional information of the detected marker, so that the radiation irradiation of the radiation corresponding to movement of the tumor can be performed with a high-degree of accuracy. When the positional information of such a marker is obtained, template matching utilizing a template is executed.

Meantime, a (fiducial) marker must be inserted and implanted in advance inside the body of the subject to detect the movement of the tumor utilizing the marker set forth above. On the other hand, recently a markerless (non-marker) tracking without implanting the marker is proposed, in which a specific region such as the patient's tumor area is used instead of the marker.

RELATED PRIOR ART DOCUMENTS

Patent Document

Patent Document 1—JP Patent 3053389 B1

ASPECTS AND SUMMARY OF THE INVENTION

Objects to be Solved

With regard to the marker tracking using the template matching, a template is prepared by selecting the marker region which is visually recognizable in a high-level. On the other hand, when applying the markerless tracking, the template is prepared by selecting the position of the specific region. However, in many cases, the specific region in the fluoroscopic radiograph is poorly recognizable. For example, the specific region such as a tumor in a liver and a pancreas is hardly recognized by eye. On the other hand, such organs move more or less along with breathing of the subject even not as much as a lung, so that the position of the specific region should be tracked by any means. Therefore, with regard to the liver and the pancreas, tracking the exact position of the specific region thereof is quite arduous and as a result, the accuracy of template matching worsens. On the other hand, it is problematic that implanting the marker in the liver and the pancreas is too difficult to perform marker-tracking at all.

In addition, the template must be prepared just before the therapy to perform the template matching and the subject must wait for such a preparation while being fixed with a fixture on the examination table, and as results, it is problematic that not only the subject is painful, but also throughput of the radiotherapy worsens.

The purpose of the present invention is to solve the above objects and to provide a radiotherapy tracking apparatus that tracks the position of the specific region with markerless tracking even when visual recognition of the specific region of the subject is poor and eliminates an advance work such as preparation of the template.

Means for Solving the Problem

According to the first invention, a radiotherapy tracking apparatus (tracking apparatus for radiotherapy) that detects respiratory phases of a subject and tracks movement of a specific region of the subject, comprises: a digitally reconstructed radiographic (DRR) image generation element (circuit) that generates a plurality of DRR images including the specific region throughout an entire respiratory phase by performing a virtual fluoroscopic projection simulating a geometric fluoroscopic condition between an X-ray tube and an X-ray detector relative to a four-dimensional CT (computed tomographic) image data comprising a group consisting of three-dimensional CT data, which are generated during a therapy planning, of regions including (covering) the specific region in a plurality of continuous respiratory phases of the subject; a phase-based position calculation that calculates a position of the specific region in a plurality of DRR images every respiratory phase (from phase to phase) of the subject based on the position of the specific region that is registered in the four-dimensional CT image data of the subject, which is created during the therapy planning; an X-ray fluoroscopic image obtaining element that obtains an X-ray fluoroscopic image having a plurality of frames including the specific region of the subject relative to the entire respiratory phase of the subject by continuously collecting the X-ray fluoroscopic image acquired by that the X-ray detector detects the X-ray that is irradiated from the X-ray tube and transmits through the subject; a phase adjustment element that coordinates the plurality of the DRR images generated every respiratory phase of the subject by the DRR image generation element relative to the X-ray fluoroscopic image having the plurality of frames acquired by the X-ray fluoroscopic image obtaining element with the respiratory phase of the subject; a frame-based position calculation element that calculates the position of the specific region of the subject in the X-ray fluoroscopic image having the plurality of frames, every frame based on the DRR image coordinated with the X-ray fluoroscopic image in the phase adjustment element and the position of the specific region in the DRR image calculated by the phase-based calculation element.

According to the second invention, the phase adjustment element coordinates the plurality of the DRR images and the X-ray fluoroscopic image having the plurality of frames based on the similarity level between the DRR image and the X-ray fluoroscopic image.

According to the third invention, the phase adjustment element extracts the plurality of feature points in the plurality of the DRR images and a plurality of feature points of the X-ray fluoroscopic images having the plurality of frames and then, adjusts (coordinates) while understanding that the DRR image having the least difference between the position of the plurality of feature points in the DRR image and the position of the plurality of feature points corresponding to the plurality of feature points in the DRR images relative to the X-ray fluoroscopic image and the X-ray fluoroscopic images adjust (coordinate) with the respiratory phase of said subject.

According to an aspect of the fourth invention, the phase adjustment element coordinates while understanding that the DRR image having the least sum of square of the difference between the position of the plurality of feature points in the DRR image and the position of the plurality of feature points corresponding to the plurality of feature points in the DRR image and the X-ray fluoroscopic image adjust with the respiratory phase of the subject.

According to an aspect of the fifth invention, the number of plurality of the DRR images is smaller than the number of the X-ray fluoroscopic image having the plurality of frames, and the phase adjustment element adjusts the position of the specific region in the DRR image with the X-ray fluoroscopic image having the plurality of frames following utilizing and interpolating the DRR images having the adjacent phase to each other.

Effect of the Invention

According to the aspects of the first invention and the second invention, the position of the feature point is tracked with markerless tracking in the high-degree of accuracy even when the visual recognition of the specific region of the subject is poor. In addition, the workload such as an advance preparation of the template is no longer mandatory, so that the throughput of the radiation therapy is improved.

The third invention and the forth invention facilitates the adjustment between the DRR image and the X-ray fluoroscopic image in a high-degree of accuracy utilizing the positions of the plurality of feature points of the DRR image and the positions of the plurality of feature points of the X-ray fluoroscopic image.

According to an aspect of the fifth invention, even when the number of a plurality of the DRR images is smaller than the number of the X-ray fluoroscopic image having the plurality of frames, and the position of the specific region is coordinated with the X-ray fluoroscopic image having the plurality of frames based on interpolating.

The above and other aspects, features and advantages of the present invention will become apparent from the following description read in conjunction with the accompanying drawings, in which like reference numerals designate the same elements.

DETAILED DESCRIPTION OF THE PREFERRED EMBODIMENTS

Figure 1:
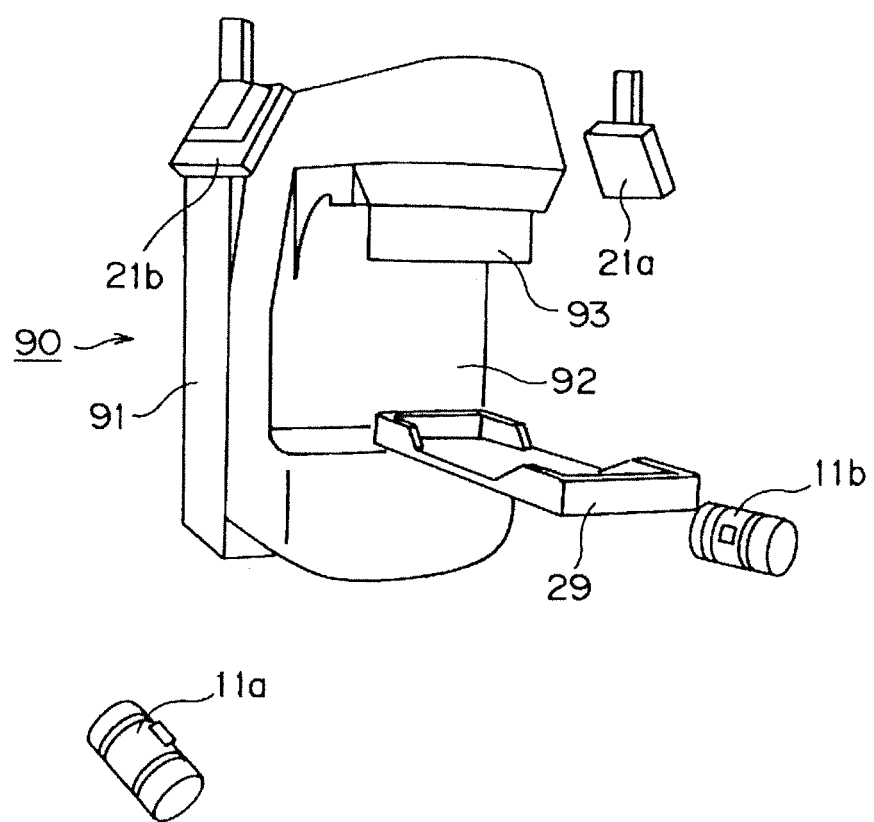
FIG. 1 is a perspective view of a radiotherapy tracking apparatus of the present invention together with a radiation irradiation device 90.

Reference will now be made in detail to embodiments of the invention. Wherever possible, same or similar reference numerals are used in the drawings and the description to refer to the same or like parts or steps. The drawings are in simplified form and are not to precise scale. The word 'couple' or 'connect' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

The inventor sets forth Embodiments of the present invention based on the following FIGS. FIG. 1 is a perspective view of a radiotherapy tracking apparatus of the present invention together with a radiation irradiation device 90. The radiation irradiation device comprises such a radiotherapy tracking apparatus and such a radiation irradiation device 90.

The radiation irradiation device 90 that irradiates the radiation relative to the subject on the examination table, also called couch, 29 comprises a gantry 92 oscillable (swingable) relative to the couch base (pedestal) 91 installed on the floor of the therapy room, and a head 93 that is mounted to the gantry 92 and emits the therapeutic beam. Such radiation irradiation device 90 changes the irradiation direction of the therapeutic beam irradiated from the head 93 by swinging (oscillating) the gantry 92 relative to the couch base 91. Consequently, the therapeutic beam can be irradiated from a variety of directions to the affected area such as a tumor and so forth of the subject.

The radiotherapy tracking apparatus used together with such radiation irradiation device 90 executes an X-ray fluoroscopy to perform a dynamic tracking to identify the position of the affected area of the subject. Specifically, when performing such radiation therapy using the radiation irradiation device 90, the radiation must be accurately irradiated to the affected area that moves along with the body movement of the subject. Therefore, the specific region is detected in a high-degree of accuracy by pre-registering the region having a specific shape, such as a tumor of the subject, performing continuously an X-ray fluoroscopy and calculating the three-dimensional position information of the specific region, so that called a dynamic tracking is performed to detect the specific region in a high-degree of accuracy. In such a way, a dynamic tracking method, in which an image of the specific region such as e.g., a tumor of the subject is used as a marker instead of a conventional maker implanted near the affected area of the subject, is called markerless tracking.

Such a radiotherapy tracking apparatus comprises a first X-ray tube 11a and a second X-ray tube 11b, and a first flat panel detector 21a and a second flat panel detector 21b. X-ray irradiated from the first X-ray tube 11a transmits the subject on the examination table 29 and subsequently, is detected by the first flat panel detector 21a. A first X-ray radiography system comprises the first X-ray tube 11a and the first flat panel detector 21a. X-ray irradiated from the second X-ray tube 11b transmits the subject on the examination table 29 and subsequently, is detected by the second flat panel detector 21b. A second X-ray radiography system comprises the second X-ray tube 11b and the second flat panel detector 21b.

Figure 2:
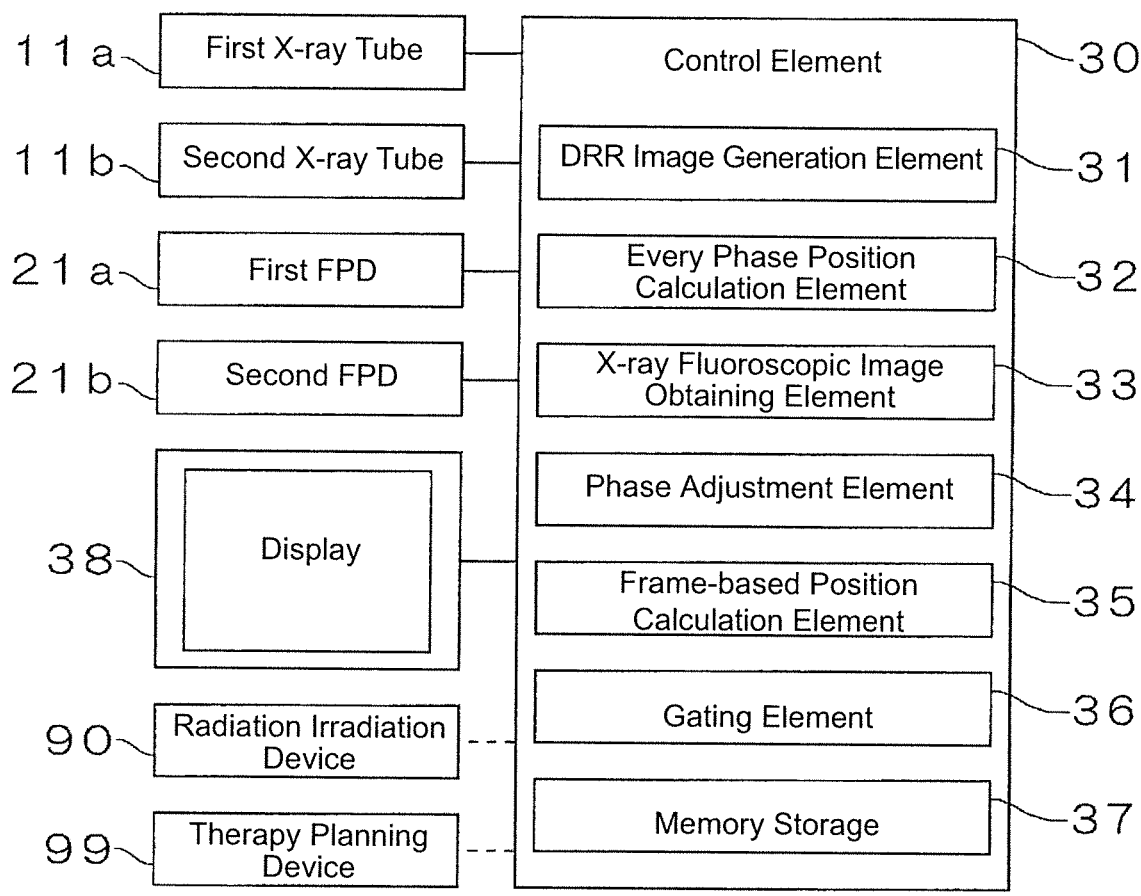
FIG. 2 is a block diagram illustrating the main control system of the radiotherapy tracking apparatus according to an aspect of the present invention.

FIG. 2 is a block diagram illustrating the principal (main) control system of the radiotherapy tracking apparatus according to an aspect of the present invention.

Such an X-ray fluoroscopic apparatus comprises: a CPU as a processor that executes the logic operation; a ROM that stores operation programs required to control the apparatus; a RAM that stores temporally the data and so forth when controlling and so forth; and further comprises: a control element 30 that controls the entire apparatus. The control element 30 is connected, as described above, to the first X-ray tube 11a, the second X-ray tube 11b, the first flat panel detector 21a and the second flat panel detector 21b. In addition, the control element 30 is connected to a display 38 consisting of the liquid crystal display panel and so forth.

The control element 30 comprises, as a variety of functional elements, a DRR image generation element 31, a phase-based position calculation element 32, an X-ray fluoroscopic image obtaining element 33, a phase adjustment element 34, an every frame position calculation element 35, a gating element 36 and a memory storage element 37.

The DRR image generation element 31 generates a plurality of the DRR images, including the specific region, relative to all respiratory phases of the subject by performing a virtual fluoroscopic projection simulating the geometric fluoroscopy condition between the first X-ray radiography system comprising the first X-ray tube 11a and the first flat panel detector 21a and the second X-ray radiography system comprising the second X-ray tube 11b and the second flat panel detector 21b relative to the four-dimensional CT image data, which is created on the therapy planning. Now, the four-dimensional CT image data is a CT image data comprising a group of 3-dimensional CT image data relative to a plurality of continuous respiratory (breathing) phases of the subject, which is created on the therapy planning. Such DRR images are stored in the memory storing element 37.

The phase-based position calculation element 32 calculates a position of the specific region in a plurality of DRR images every respiratory phase of the subject based on the position of the specific region that is registered in the four-dimensional CT image data of the subject, which is created during the therapy planning. Specifically, when creating the therapy planning, the medical technician adds the positional data relative to the tumor position relative to the CT image data. The position of the specific region in the DRR image relative to each phase is calculated in advance using such positional data based on the geometric fluoroscopy condition set forth above. Such a position of the specific region is stored in the memory storing element 37.

The X-ray fluoroscopic image obtaining element 33 acquires an X-ray fluoroscopic image having a plurality of frames including the specific region of the subject relative to the entire respiratory phase of the subject by continuously collecting the X-ray fluoroscopic image taken using the above first X-ray imaging system and the above second X-ray imaging system. Such X-ray fluoroscopic images are stored in the memory storing element 37.

The phase adjustment element 34 adjusts (coordinates) the plurality of the DRR images generated every respiratory phase of the subject by the DRR image generation element 31 relative to the X-ray fluoroscopic image having the plurality of frames obtained by the X-ray fluoroscopic image obtaining element 33 with the respiratory phase of the subject.

The every frame position calculation element 35 calculates the position of the specific region of the subject in the X-ray fluoroscopic image having the plurality of frames, frame-by-frame, based on the DRR image coordinated with the X-ray fluoroscopic image by the phase adjustment element 34 and the position of the specific region in the DRR image calculated and adjusted by the phase-based position calculation element 32.

The gating element 36 sends the irradiation signal of the therapeutic beam to the radiation irradiation device 90 when the position of the specific region of the subject in the X-ray image, having a plurality of frames, calculated by the frame-based position calculation element 35 is placed in the irradiation area of the therapeutic beam, set up in advance on the therapy planning.

Figure 3:
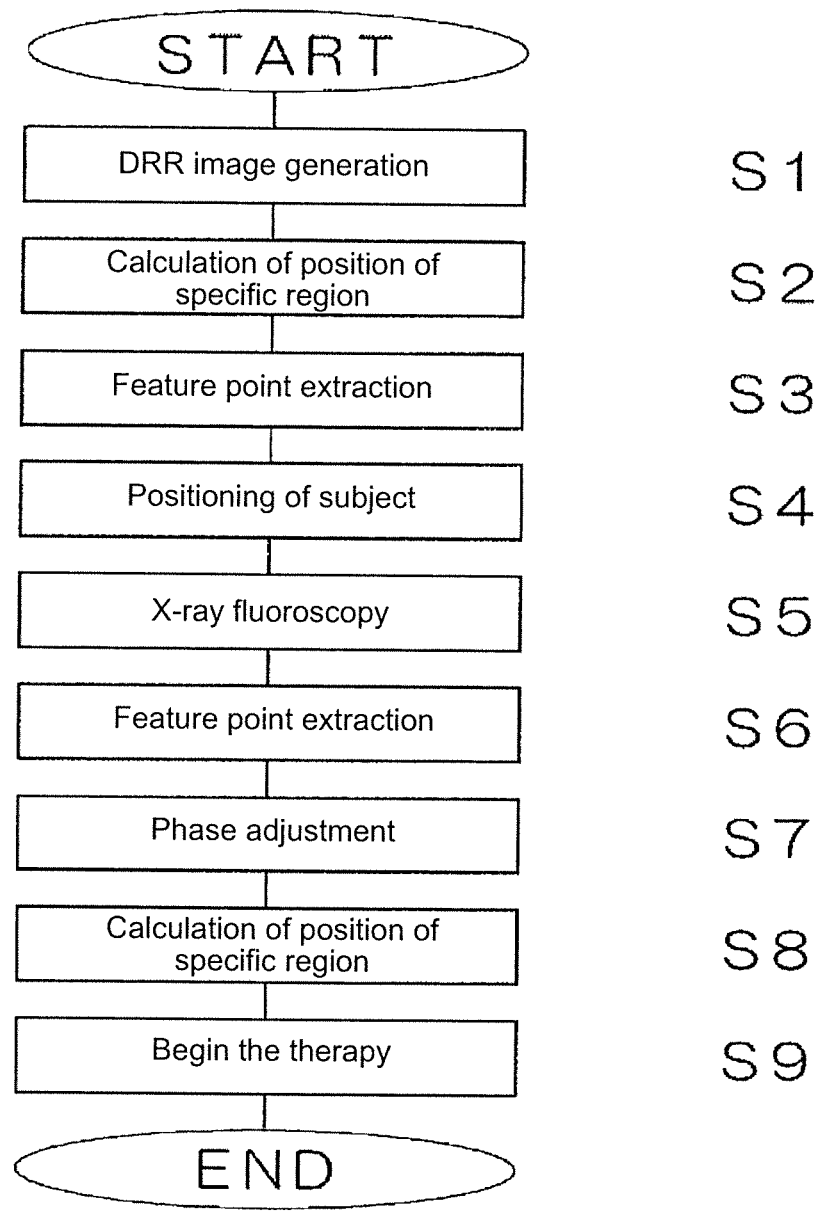
FIG. 3 is a flow-chart illustrating a dynamic tracking operation relative to the radiotherapy tracking apparatus according to the aspect of the present invention.

Next, the inventors set forth a dynamic tracking operation that tracks the position of the specific region of the subject by the radiotherapy tracking apparatus comprising the above structure. FIG. 3 is the flow-chart illustrating the dynamic tracking operation relative to the radiotherapy tracking apparatus according to the aspect of the present invention.

In addition, the following operations are executed on both first X-ray imaging system comprising the first X-ray tube 11a and the first flat panel detector 21a and second X-ray imaging system comprising the second X-ray tube 11b and the second flat panel detector 21b.

When executing the dynamic tracking that tracks the position of the specific region of the subject, a DRR image is firstly generated in the preparatory step (Step S1). The DRR image generation element 31 generates a plurality of the DRR images, including the specific region, relative to all respiratory phases of the subject by performing a virtual fluoroscopic projection simulating the geometric fluoroscopy condition between the first X-ray imaging system comprising the first X-ray tube 11a and the first flat panel detector 21a and the second X-ray imaging system comprising the second X-ray tube 11b and the second flat panel detector 21b relative to the four-dimensional CT image data, including the specific region of the subject, which is created by the therapy planning device 99 on the therapy planning. Such DRR images are stored in the memory storing element 37.

Next, the position of the specific region in the plurality of DRR images is calculated (Step S2). When the therapy planning is created, the position of the specific region in the four-dimensional CT image data of the subject is pre-registered. The phase-based position calculation element 32 calculates a position of the specific region in a plurality of DRR images every respiratory phase of the subject based on the position of the specific region that is registered in the four-dimensional CT image data of the subject, which is created during the therapy planning. Such a position of the specific region is stored in the memory storing element 37.

Next, the feature point is extracted from the DRR image, which the DRR image generation element 31 generates, that is stored in the memory storage element 37 (Step S3).

Figure 4A:
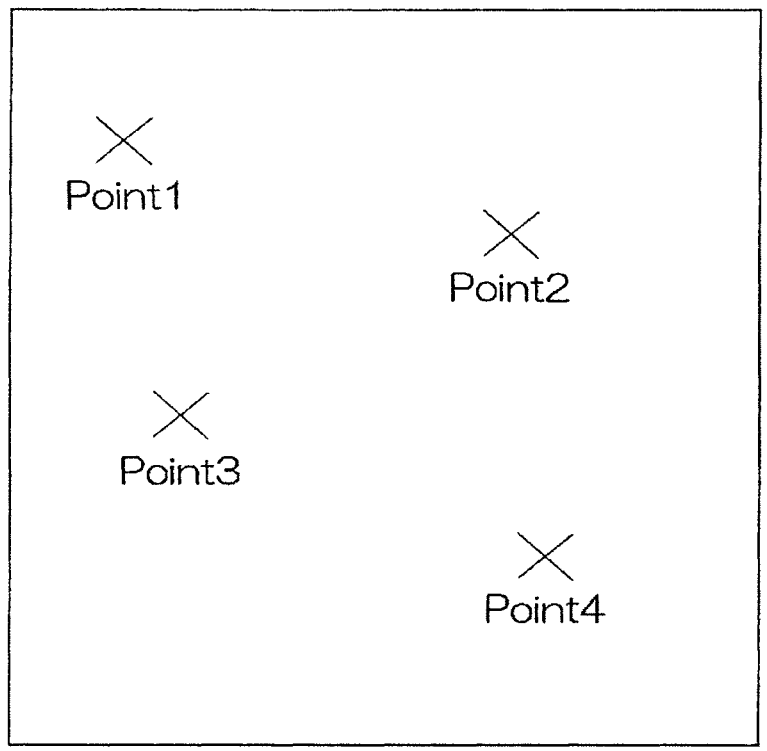
FIG. 4A, 4B are schematic views illustrating the aspect in which the feature points Point 1-Point 4 are selected from the DRR image and stored in the memory.
Figure 4A:
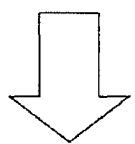
Figure 4B:
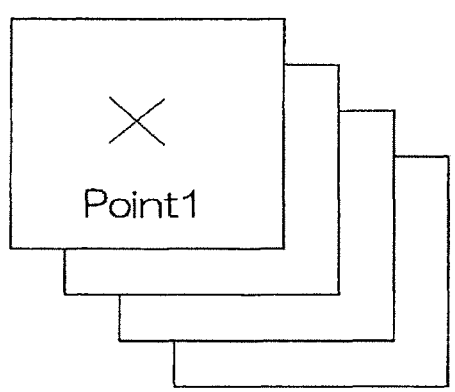

FIG. 4A, 4B are schematic views illustrating the aspect in which the feature points Point 1-Point 4 are selected from the DRR image and stored in the memory.

FIG. 4A, 4B are illustrating the aspect in which the four feature points Point 1-Point 4 are extracted from the DRR image every respiratory phase of the subject, which the DRR image generation element 31 generates. In practice, much more feature points are extracted. Such feature points are extracted from not only the specific region of the subject, but also from the entire DRR image. Accordingly, even when the specific region of the subject is hardly recognized in the DRR image, the extraction of the feature point is feasible using the other region. Such feature points are extracted by executing an image processing on the DRR image. And referring to FIGS. 4A, 4B, the adjustment (coordination) of the extracted feature points Point 1-Point 4 and the pattern of the periphery of the feature points Point 1-Point 4 are stored in the memory storage element 37.

As such feature points, for example, a protrusion of bone, a featured branching pattern of the bronchial tube and so forth, which can be a characteristic structure, are extracted as a feature point. Here, such feature points are selected from the regions moving along with the respiration of the subject. The feature point is not extracted from an abdomen of the subject, which is the region subject to a peristaltic movement not related to the respiratory phase. Such a region along with the respiratory movement can be selected automatically by the device or manually by the operator.

In addition, the extraction of the feature point from the DRR image can be executed when generating the DRR image as set forth above, but also can be executed at the same time, in real time, when coordinating the phase with the X-ray fluoroscopic image as set forth later.

Once the above steps are completed, the subject is positioned at the position in which the therapeutic beam is irradiated using the four-dimensional CT image data generated on the therapy planning following loading the subject on the examination table 29 (Step S4).

In addition, X-ray fluoroscopies from two different directions to each other relative to the subject are executed, using both the first X-ray imaging system comprising the first X-ray tube 11a and the first flat panel detector 21a and the second X-ray imaging system comprising the second X-ray tube 11b and the second flat panel detector 21b (Step S5). At the step S5, the X-ray fluoroscopic image is continuously acquired at the frame rate, e.g., approximately 30 fps (frame per second). Such X-ray fluoroscopic images are stored in the memory storing element 37.

Next, the feature point is extracted from the X-ray fluoroscopic image that is stored in the memory storage element 37 (Step S6).

At the step S6, the feature point in the X-ray fluoroscopic image corresponding to the same region as the feature points Point 1-Point 4 that are extracted in the DRR image by performing the pattern matching relative to the X-ray fluoroscopic image, using the pattern of the peripheries of the feature points Point 1-Point 4 that are extracted in the DRR image, is extracted. At the step S6, the feature points that are extracted in the DRR image and are not adjacent to each other are utilized, and the corresponding feature point can be easily extracted by executing the pattern matching relative to the points having a close coordinate to each other. In addition, for example, the normalized correlation of pixel values can be applied to the method for the pattern matching at the step S6.

And, while executing the X-ray fluoroscopy, the feature points corresponding to the same region of the subject in the X-ray fluoroscopic images having the plurality of frames are coordinated with each other by tracking the feature point extracted in the X-ray fluoroscopic image. Such a tracking uses the information relative to the movement rate or the acceleration rate. In addition, the pattern matching every frame can be executed instead of tracking the feature point.

The plurality of the DRR images generated every respiratory phase of the subject by the DRR image generation element 31 relative to the X-ray fluoroscopic image having the plurality of frames acquired by the X-ray fluoroscopic image obtaining element 33 are coordinated with the respiratory phase of the subject while executing the acquisition of such X-ray fluoroscopic images and the extraction of the feature points (Step S7). Specifically, the X-ray fluoroscopic image and the DRR image are coordinated with each other every time when acquiring the X-ray fluoroscopic image having one frame. Therefore, the adjustment of the phases is executable even when the X-ray fluoroscopic image having the frame corresponding to all respiratory phases of the subject.

At the step S7, a plurality of the DRR images and the X-ray fluoroscopic image having the plurality of frames are coordinated based on the similarity level between the DRR image and the X-ray fluoroscopic image. More specifically, when the X-ray fluoroscopic image and the DRR image are coordinated, the sum of squares of the distance between the feature point in each X-ray fluoroscopic image and the feature point coordinated with the feature point in the X-ray fluoroscopic image relative to each DRR image generation element 31 is calculated and it is recognized in that the X-ray fluoroscopic image and the DRR image providing the least sum of squares coordinate with the respiratory phase.

More specifically, given A, is a coordinate of the feature point in the X-ray fluoroscopic image, $a_{k,i}$ is a coordinate of the feature point in the DRR image, i is a numeric number of the feature point, N is the number of the feature points, and k is a respiratory phase (time phase) of the DRR image, it is recognized that a phase relative to the DRR image providing the least value relative to the value denoted by the following formula coordinates with a phase of the X-ray fluoroscopic image.

$$\min_{k} \sum_{i=1}^{N} \|A_i - a_{k,i}\|^2 \qquad \text{Mathematical Expression I}$$

Here, the coordinate of the feature point uses a relative coordinate, for example, the relative coordinate having the median point of all feature points as the original point (starting point) is applied to respective DRR images and X-ray fluoroscopic images. Therefore, even when the entire image translates between the DRR image and the X-ray fluoroscopic image, it is prevented that the sum of squares of the distance is too large, and as a result, the adjustment of the phases is executed precisely (accurately).

Next, the position of the specific region in the subject is calculated (Step S8). At the step 8, the every frame position calculation element 35 calculates the position of the specific region of the subject in the X-ray fluoroscopic image having the plurality of frames every frame based on the DRR image coordinated with the X-ray fluoroscopic image in the phase adjustment element 34 and the position of the specific region in the DRR image calculated by the phase-based position calculation element 32. Specifically, it is found that the position of the specific region of each X-ray fluoroscopic image coincides with the position of the specific region corresponding thereto of the DRR image.

While performing the X-ray fluoroscopy, when the position of the specific region is trackable by continuously executing the position calculation of the specific region of the subject, the radiotherapy begins (Step S9). At the step S9, the gating element 36 sends the irradiation signal of the therapeutic beam to the radiation irradiation device 90 when the position of the specific region of the subject in the X-ray image having a plurality of frames, which is calculated by the every frame position calculation element 35, is in-place in the irradiation area of the therapeutic beam, which is set up in advance on the therapy planning.

As set forth above, according to the aspect of the present invention, the radiotherapy tracking apparatus calculates the position of the specific region of the subject in the X-ray fluoroscopic image having the plurality of frames every frame based on the DRR image coordinated with the X-ray fluoroscopic image and the position of the specific region in such a DRR image, so that the position of the specific region is trackable in a high-degree of accuracy using the markerless tracking even when the visual recognition relative to the specific region of the subject is poor. In addition, the workload such as an advance preparation of the template and so forth is no longer mandatory; so that the painfulness of the subject is alleviated, and the throughput of the radiation therapy is improved.

In addition, generally, the number of the DRR images generated relative to the one respiratory phase of the subject is commonly smaller than the number of the X-ray fluoroscopic images generated relative to the one respiratory phase of the subject. Specifically, for example, approximately 10 DRR images are generated per e.g., one respiratory phase of the subject. In contrast, given the frame rate of the X-ray fluoroscopy is 30 fps and one breathing of the subject takes place every 4 seconds, the X-ray fluoroscopic image having 120 frames is generated. Accordingly, the phase of the DRR image and the phase of the X-ray fluoroscopic image are not in a one-to-one relationship. Therefore, the structure, in which the phase adjustment element 34 coordinates the position of the specific region in the DRR image with the X-ray fluoroscopic image having the plurality of frames following interpolating relative to the DRR images having the adjacent phase each other, is adopted.

Figure 5:
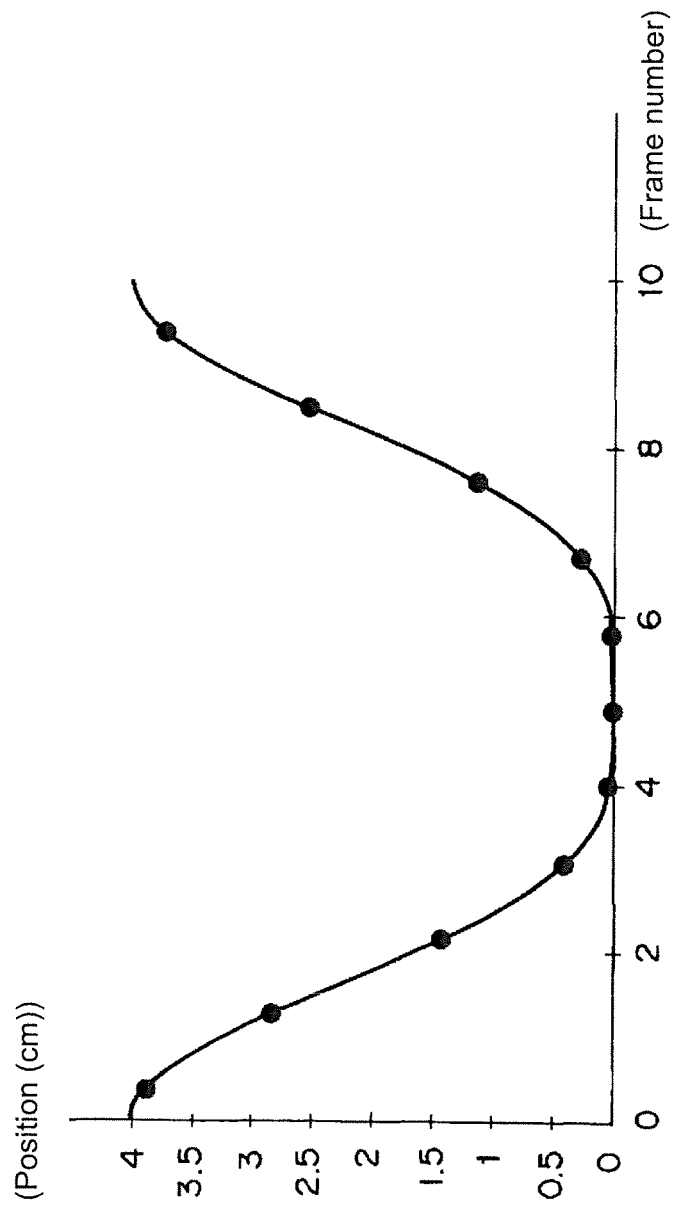
FIG. 5 is a graph illustrating an available periodic function when executing interpolation.

FIG. 5 is a graph illustrating an available periodic function when executing such an interpolation.

Such a graph is illustrating a hypothetical case in which 10 frames of the DRR image every constant time are generated during one cycle of breathing of the subject. In such a graph, the vertical axis denotes a position (distance cm) of the specific region in the DRR image in the y-direction from the baseline (reference 0 cm) that is the position of the specific region when the respiratory phase of the subject is the maximum respiratory phase and the horizontal axis denotes each respiratory phase (i.e., the frame number of the DRR image generated based on the four-dimensional CT image data). Here, the y-direction is a principal movement direction of the specific region. The specific region moves in the X-, Y-direction in the DRR image, but only the position in the Y-direction in each DRR image is illustrated in FIG. 5. The position in the X-direction is the same as in FIG. 5.

The position of the specific region in the DRR image every respiratory phase of the subject is interpolated in a high-degree of accuracy utilizing the periodic function related to the respiratory phase referring to FIG. 5. And, when coordinating the DRR image with X-ray fluoroscopic image, an accurate respiratory phase is calculated by weighing based on the sum of squares utilizing the DRR image providing the least sum of squares, as set forth above, and the DRR image providing the second least sum of squares and then, the position of the specific region is calculated in a high-degree of accuracy from the regression function using such a calculated accurate respiratory phase.

When such a structure is applied, even when the number of plurality of the DRR images is smaller than the number of the X-ray fluoroscopic image having the plurality of frames, the position of the specific region is coordinated with the X-ray fluoroscopic image having the plurality of frames based on an interpolating.

In addition, according to the aspect of the Embodiment set forth above, when the structure, in which the irradiation signal of the therapeutic beam is sent when the position of the specific region of the subject in the X-ray image is in-place in the irradiation area of the therapeutic beam, is adopted and in addition, the structure, in which the adjustment relative to the X-ray fluoroscopic image having a plurality of frames is executed following interpolation relative to the DRR images adjacent to each other, is adopted, the position of the specific region is trackable in a high-degree of accuracy. Regardless, it is feasible that the irradiation signal of the therapeutic beam relative to the radiation irradiation device 90 is sent based on the respiratory phase.

Specifically, without particularly calculating the position of the specific region, the position of the specific region recognizes the respiratory phase included in the predetermined range and when the subject is in such a respiratory phase, the irradiation signal of the therapeutic beam can be sent to the radiation irradiation device 90. The respiratory phase to carry out irradiation of the therapeutic beam is specified on the therapy planning, so that the therapeutic beam can be irradiated when being in the range of such a respiratory phase.

As used herein, a computer system broadly includes some form of an input device for receiving data, an output device for outputting data in tangible form (e.g. printing or transmitting data, or displaying on a computer screen), a memory for storing data as well as computer code, and a processor/ microprocessor for executing computer code wherein said computer code resident in the memory will physically cause said processor/microprocessor to read-in data via said input device, process said data within said microprocessor and output said processed data via said output device.

It will be further understood by those of skill in the art that the apparatus and devices and the elements herein, without limitation, and including the sub components such as operational structures, circuits, communication pathways, and related elements, control elements of all kinds, display circuits and display systems and elements, any necessary driving elements, inputs, sensors, detectors, memory elements, processors and any combinations of these structures etc. as will be understood by those of skill in the art as also being identified as or capable of operating the systems and devices and subcomponents noted herein and structures that accomplish the functions without restrictive language or label requirements since those of skill in the art are well versed in related radiotherapy tracking devices, systems, and arrangements, including related radiotherapy tracking computers and operational controls and technologies of radiographic devices and all their sub components, including various circuits and components and combinations of circuits and combinations of components without departing from the scope and spirit of the present invention.

Although only a few embodiments have been disclosed in detail above, other embodiments are possible and the inventors intend these to be encompassed within this specification. The specification describes certain technological solutions to solve the technical problems that are described expressly and inherently in this application. This disclosure describes embodiments, and the claims are intended to cover any modification or alternative or generalization of these embodiments which might be predictable to a person having ordinary skill in the art.

Those of skill would further appreciate that the various illustrative logical blocks, modules, operating circuits, and algorithm steps described in connection with the embodiments disclosed herein may be implemented as electronic hardware, computer software running on a specific purpose machine that is programmed to carry out the operations described in this application, or combinations of both. To clearly illustrate this interchangeability of hardware and software, various illustrative components, blocks, modules, circuit illustrations, step-modes, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the exemplary embodiments.

The various illustrative logical blocks, modules, and circuits described in connection with the embodiments disclosed herein, may be implemented or performed with a general or specific purpose processor, or with hardware that carries out these functions, e.g., a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. The processor can be part of a computer system that also has an internal bus connecting to cards or other hardware, running based on a system BIOS or equivalent that contains startup and boot software, system memory which provides temporary storage for an operating system, drivers for the hardware and for application programs, disk interface which provides an interface between internal storage device(s) and the other hardware, an external peripheral controller which interfaces to external devices such as a backup storage device, and a network that connects to a hard wired network cable such as Ethernet or may be a wireless connection such as a RF link running under a wireless protocol such as 802.11. Likewise, an external bus may be any of but not limited to hard wired external busses such as IEEE-1394 or USB. The computer system can also have a user interface port that communicates with a user interface, and which receives commands entered by a user, and a video output that produces its output via any kind of video output format, e.g., VGA, DVI, HDMI, display port, or any other form. This may include laptop or desktop computers, and may also include portable computers, including cell phones, tablets such as the IPAD™ and Android™ platform tablet, and all other kinds of computers and computing platforms.

A processor may also be implemented as a combination of computing devices, e.g., a combination of a DSP and a microprocessor, a plurality of microprocessors, one or more microprocessors in conjunction with a DSP core, or any other such configuration. These devices may also be used to select values for devices as described herein.

The steps of a method or algorithm described in connection with the embodiments disclosed herein may be embodied directly in hardware, in a software module executed by a processor, using cloud computing, or in combinations. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of tangible storage medium that stores tangible, non-transitory computer based instructions. An exemplary storage medium is coupled to the processor such that the processor can read information from, and write information to, the storage medium. In the alternative, the storage medium may be integral to the processor. The processor and the storage medium may reside in reconfigurable logic of any type.

Those of skill in the particular art will be recognized as having and having access to sophisticated radiotherapy tracking systems, circuits, and methods such that the skill level is high in science, technology, computers, programming, circuit design, and arrangement such that the described elements herein, after and following a review of this inventive disclosure and the inventive details herein, will be understood by those of skill in the art.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer.

The memory storage can also be rotating magnetic hard disk drives, optical disk drives, or flash memory based storage drives or other such solid state, magnetic, or optical storage devices. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media. The computer readable media can be an article comprising a machine-readable non-transitory tangible medium embodying information indicative of instructions that when performed by one or more machines result in computer implemented operations comprising the actions described throughout this specification.

Operations as described herein can be carried out on or over a web site. The website can be operated on a server computer, or operated locally, e.g., by being downloaded to the client computer, or operated via a server farm. The website can be accessed over a mobile phone or a PDA, or on any other client. The website can use HTML code in any form, e.g., MHTML, or XML, and via any form such as cascading style sheets ("CSS") or other.

The computers described herein may be any kind of computer, either general purpose, or some specific purpose computer such as a workstation. The programs may be written in C, or Java, Brew or any other programming language. The programs may be resident on a storage medium, e.g., magnetic or optical, e.g. the computer hard drive, a removable disk or media such as a memory stick or SD media, or other removable medium. The programs may also be run over a network, for example, with a server or other machine sending signals to the local machine, which allows the local machine to carry out the operations described herein.

Also, the inventors intend that only those claims which use the words "means for" (specifically including the phrase "for" in "means for") are intended to be interpreted under 35 USC 112 (f). Moreover, no limitations from the specification are intended to be read into any claims, unless those limitations are expressly included in the claims.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

REFERENCE OF SIGNS

11a First X-ray tube
11b Second X-ray tube
21a First flat panel detector
21b Second flat panel detector
29 Examination table
30 Control element
31 DRR image generation element
32 Every phase position calculation element
33 X-ray fluoroscopic image obtaining element
34 Phase adjustment element
35 Frame-based position calculation element
36 Gating element
37 Memory storage element
38 Display
90 Radiation irradiation device
99 Therapy planning device

What is claimed is:

1. A radiotherapy tracking apparatus for detecting a respiratory phase of a subject and tracking movement of a specific region of said subject, comprising:
a digitally reconstructed radiographic (DRR) image generation element that performs a virtual fluoroscopic projection to a four-dimensional computed tomographic (CT) image data group, wherein the virtual fluoroscopic projection is such that therein a fluoroscopic condition is geometrically reproduced between an X-ray tube and an X-ray detector, the four-dimensional computed tomographic (CT) image data group consisting of three-dimensional CT data that are generated during a therapy planning and that covers said specific region in a plurality of continuous respiratory phases of said subject, thereby generating a plurality of DRR images covering said specific region throughout an entire respiratory phase of said subject;
a phase-based position calculation element that calculates a position of said specific region in a plurality of DRR images for each respiratory phase of said subject, based on said position of said specific region, wherein said position is preliminary registered in said four-dimensional CT image data of said subject during the therapy planning;
an X-ray fluoroscopic image obtaining element that continuously obtains X-ray fluoroscopic images by means of said X-ray detector detecting X-ray that is generated from said X-ray tube and transmits through said subject, thereby obtaining a plurality of X-ray fluoroscopic images each including said specific region of said subject through said entire respiratory phase of said subject; a phase adjuster that correlates said plurality of said DRR images generated for each respiratory phase of said subject by said DRR image generation element with said X-ray fluoroscopic image having said plurality of X-ray fluoroscopic images obtained by said X-ray fluoroscopic imaging apparatus in accordance with the respiratory phase of said subject; and
a frame-based position calculation element that calculates said position of said specific region of said subject in said X-ray fluoroscopic image having said plurality of frames frame-by-frame based on said DRR image adjusted with said X-ray fluoroscopic image in said phase adjuster and said position of said specific region calculated by said phase-based position calculation element.

2. The radiotherapy tracking apparatus, according to claim 1, wherein:
said phase adjuster adjusts the plurality of said DRR images and the X-ray fluoroscopic image having the plurality of frames based on a similarity level between said DRR image and said X-ray fluoroscopic image.

3. The radiotherapy tracking apparatus, according to claim 1, wherein:
said phase adjuster extracts a plurality of feature points in a plurality of said DRR images and a plurality of feature points of said X-ray fluoroscopic images having said plurality of frames and then, determines and adjusts that said DRR image having the least difference between the position of said plurality of feature points in said DRR image and said position of said plurality of feature points corresponding to said plurality of feature points in said DRR images in said X-ray fluoroscopic image and said X-ray fluoroscopic images adjust with said respiratory phase of said subject.

4. The radiotherapy tracking apparatus, according to claim 3, wherein:
said phase adjuster determines and adjusts that said DRR image having the least sum of squares of said difference between the position of said plurality of feature points in said DRR image and said position of said plurality of feature points corresponding to said plurality of feature points in said DRR images in said X-ray fluoroscopic image and said X-ray fluoroscopic images adjust with said respiratory phase of said subject.

5. The radiotherapy tracking apparatus, according to claim 1, wherein:
a number of said plurality of DRR image is smaller than a number of said X-ray fluoroscopic image having said plurality of frames, and said phase adjuster adjusts the position of said specific region in the DRR image with the X-ray fluoroscopic image having said plurality of frames following utilizing and interpolating said DRR images having an adjacent phase to each other.

* * * * *